United States Patent
Pujado (12)

(10) Patent No.: US 6,596,244 B1
(45) Date of Patent: *Jul. 22, 2003

(54) FALLING FILM REACTOR WITH CORRUGATED PLATES

(75) Inventor: Peter R. Pujado, Kildeer, IL (US)

(73) Assignee: UOP LLC, Des Plaines, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/316,714

(22) Filed: May 21, 1999

Related U.S. Application Data (62) Division of application No. 08/967,137, filed on Nov. 10, 1997, now Pat. No. 5,922,903.

(51) Int. Cl.[7] .............................. B01D 1/22; F28D 7/08; F28D 3/00
(52) U.S. Cl. .................. 422/198; 422/211; 165/115; 165/164; 165/166; 165/167; 159/5; 159/13.1; 159/15; 159/49
(58) Field of Search ................................ 165/115, 166, 165/164, 167; 422/187, 196, 197, 198, 211; 261/112.1, 112.2; 159/5, 13.1, 15, 49

(56) References Cited

U.S. PATENT DOCUMENTS

| 3,116,972 A | 1/1964 | Bevevino et al. ............. 562/33 |
|---|---|---|
| 3,328,460 A | 6/1967 | Van der Mey ................. 562/95 |
| 3,531,518 A | 9/1970 | Ohren et al. ................. 562/123 |
| 3,535,339 A | 10/1970 | Beyer et al. .................. 549/40 |
| 3,902,857 A | 9/1975 | Van der Mey et al. ...... 422/198 |
| 3,918,917 A | 11/1975 | Ashina et al. .............. 422/197 |
| 3,925,441 A | 12/1975 | Toyoda et al. ................ 558/31 |
| 4,059,620 A | 11/1977 | Johnson ...................... 562/123 |
| 4,163,751 A | 8/1979 | Van der Mey et al. ........ 558/33 |
| 4,450,047 A | 5/1984 | Malzahn ...................... 203/15 |
| 4,706,741 A * | 11/1987 | Bolmstedt et al. .......... 165/115 |
| 5,445,801 A | 8/1995 | Pisoni ......................... 422/197 |
| 5,525,311 A | 6/1996 | Girod et al. ................. 422/200 |
| 5,538,700 A | 7/1996 | Koves ......................... 422/200 |
| 5,616,289 A * | 4/1997 | Maeda ..................... 261/112.2 |
| 6,076,598 A * | 6/2000 | Doi et al. .................... 165/166 |

* cited by examiner

Primary Examiner—Jerry D. Johnson
Assistant Examiner—Alexa A. Doroshenk
(74) Attorney, Agent, or Firm—John G. Tolomei; James C. Paschall (57) ABSTRACT

An arrangement for a falling film type reactor uses corrugated plates to improve the distribution and dispersion of the gaseous reactant into the liquid. Corrugated plates introduce increased turbulence for promoting better distribution and dispersion of the gas. Corrugation angles can be varied to suit the fluid flow properties of the liquid reactant. The reactor arrangement can also include heat transfer channels defined by the corrugated plates in an alternate arrangement of heat transfer channels and gas liquid contacting channels. The corrugations may also be varied to suit the particular heat transfer requirements of the reactions. The corrugated plates are spaced apart in the contacting channels to prevent localized film contact and placed in contact in the heat exchange portion to stabilize the plate elements defining the corrugations.

15 Claims, 5 Drawing Sheets

FALLING FILM REACTOR WITH CORRUGATED PLATES

CROSS-REFERENCE TO RELATED APPLICATION

This application is a divisional application of Ser. No. 08/967,137 filed Nov. 10, 1997, now issued as U.S. Pat. No. 5,922,903.

FIELD OF THE INVENTION

This invention relates generally to the interaction of a thin film of a liquid stream with a gaseous stream as the liquid passes down contacting surface. More specifically this invention relates to plate structures for vertical falling film contacting or removal of gaseous streams.

BACKGROUND OF THE INVENTION

Falling film evaporators and reactors are well known in the art and are readily available commercially. Falling film evaporators pass a thin film of a liquid stream down one side of a heat exchange surface in indirect heat exchange with a heating medium that contacts an opposite side of the heat exchange surface and causes an at least partial evaporation of the falling liquid. Falling film reactors comprise a plurality of tubes or plates over which a thin film of one reactant is dispersed for countercurrent or cocurrent contact with a gaseous reactant stream. In the case of evaporation or reaction laminar flow layers in the thin film can inhibit heat transfer and diffusion of vapor.

One of the most well known falling film reactor arrangements is for the continuous sulfonation or sulfation of fluid state organic substances by reaction with sulfur trioxide (sulfuric anhydride) ($SO_3$). In falling film arrangements, the $SO_3$ or other reactant is kept in a gaseous state. The reaction of the $SO_3$ with the organic substances is strongly exothermic throughout the reaction which occurs rapidly or in many cases goes nearly instantaneously to completion. The $SO_3$ is normally diluted with air or other inert gases to a reduced concentration of 4–15 wt-% which attenuates the severity of the reaction. The provision of cooling to the falling film contact surfaces also avoids the generation of temperature peaks from the highly exothermic reaction.

U.S. Pat. No. 3,925,441 issued to Toyoda et al. describes the use of flat plates for falling film sulfonation.

U.S. Pat. No. 5,445,801 to Pisoni describes a tube arrangement for falling film sulfonation that provides improved liquid distribution and accommodates expansion of the tubes.

U.S. Pat. No. 4,059,620 issued to Johnson describes the advantages of maintaining a desired heat exchange profile during the sulfonation of organic compounds with sulfur trioxide.

The sulfonation or reaction of other organic compounds can cause extensive side reactions. Side reactions are best minimized by a uniform distribution of liquid and gaseous reactions over contact surfaces. Systems for controlling the distribution into tubes or plate arrangements for falling film reactors include: weir and dam systems and slit or orifice arrangements that can be mechanically adjusted in various ways. Nevertheless, minor irregularities in the delivery systems to the top of the falling film apparatus can result in substantial flow variations with the attendant drawback of side reaction production. In addition to the problems associated with uniform delivery to a falling film contact surface, variations in the surface also create flow irregularities that can lead to non-uniform contacting and promote side reaction production.

Therefore, a reactor system is sought that will eliminate boundary layer limitations in falling film evaporators or contactors, overcome initial mal-distribution of liquid reactants in a falling film contactor and maintain an equalized distribution of reactants in a uniform film over the contact surface of the reactor.

SUMMARY OF THE INVENTION

Accordingly, an object of this invention is to provide an apparatus and process for a falling film contacting surfaces that continually redistributes the liquid film.

Another object of this invention is to provide a falling film reactor arrangement that promotes dispersion of the gaseous reactant through the thin film of liquid.

A yet further object of this invention is to provide a falling film process and arrangement that facilitates indirect heat transfer between the falling film and a heat transfer medium.

These and other objectives are achieved by a falling film device that distributes a liquid stream to a plurality of corrugated contacting columns defined in a vertical arrangement of contacting plates. The corrugations are arranged to have a primary axis that extends at least partially in a direction transverse to the vertical flow of the falling film. Movement of the fluid over the transversely extending corrugations introduces turbulence that disperses the gaseous reactants through the fluid stream for thorough and uniform contacting. Multiple corrugated plates are spaced apart across falling film contacting channels by a distance sufficient to prevent contacting of the falling film with the adjacent plates. A heat transfer fluid may be circulated to contact the sides of the corrugated plates opposite the falling film and thereby provide cooling or heating to the liquid for temperature control. Turbulence introduced by the corrugated plates will again facilitate the indirect heat transfer between the liquid film and the heat transfer medium. In this manner the corrugated plate arrangement provides advantages for the dispersion, contacting and cooling of liquid and gases in a falling film contactor arrangement.

Accordingly, in a broad process embodiment, this invention comprises a process for the contacting of a thin film liquid stream with a gaseous stream. The thin film stream passes down a plurality of corrugated surfaces defined by a plurality of vertically oriented plates. A space sufficient to prevent direct contact between adjacent films separates the adjacent plates over which the thin films descend. A gaseous stream passes through the vertical channels between the adjacent plates for dispersion into or out of the film. The process recovers a process stream from the bottom of the plates.

In another process embodiment, this invention comprises a process for the reaction of a thin film liquid stream with a gaseous reactant. The thin film stream passes down a plurality of corrugated surfaces defined by a plurality of vertically oriented plates. A space sufficient to prevent direct contact between adjacent films separates the adjacent plates over which the thin films descend. A gaseous reactant stream passes upwardly through the vertical channels between the adjacent plates for dispersion into the film. The process recovers a reaction product from the bottom of the plates.

In a more specific process embodiment, the process sulfonates organic substances by passing a stream comprising an organic liquid as a plurality of thin films down corrugated surfaces defined by a plurality of vertically oriented plates. A spacing sufficient to prevent direct contact between the films separates adjacent plates. A gaseous stream containing sulfur trioxide passes through the open vertical channels defined by the vertical plates for dispersion within the thin film. An effluent from the plates comprising a sulfonated reaction product is recovered at the bottom of the channels.

In an apparatus embodiment, this invention comprises a falling film contactor that contains a plurality of corrugated plates positioned in a parallel arrangement to define contacting channels between the adjacent plates. The plates define corrugations that extend at least partially in a horizontal direction. The adjacent plates over which the film passes have sufficient spacing to prevent contacting of liquid films passing over the surface of the adjacent plates. A distribution means provides a uniform distribution of liquid from the tops of the plates over the corrugated surfaces. An additional distribution means receives a gaseous stream through the contacting channels for dispersion into or out of the liquid descending along the plates. Means at the bottom of the plates collect a liquid stream from the contacting channels.

The process and apparatus will ordinarily employ a heat exchange fluid to control the temperature of the reactants in the falling film contactor. The heat transfer fluid passes through channels defined by the opposite side of the contacting plates over which the thin film passes. The degree of heat transfer occurring over the heat transfer surface may be varied by including heat transfer plates between contacting plates. The pitch and number of corrugations on the heat transfer plates may vary over the length of the plates and may vary with respect to the corrugations on the contacting plates to enhance and control heat transfer over the length of the contacting plates.

The arrangement of the corrugations of the contacting plates can be varied to suit the particular characteristics of the process and fluids employed. For low surface tension and low viscosity fluids, a relatively horizontal and shallow pitched corrugation is most beneficially employed. A slight downward pitch may be provided on the horizontal corrugations to provide a transverse movement of liquid and its redistribution as it travels down the reactor. The corrugation sections are preferably in a herring bone pattern so that the fluid flows back and forth in a horizontal direction across the reactor as it moves downwardly over the reactor thereby increasing the redistribution and uniformity of the downward flow. The number and height of corrugation rows can be varied in order to increase the dispersion of liquid reactant descending the corrugations. As the viscosity or surface tension of the liquid reactants in the film increases, the slope of the corrugations and depth of the corrugations may be increased to provide additional redistribution and turbulence. Preferably, any intersection or discontinuity points between corrugations are staggered horizontally to prevent collection and vertical channeling of liquid at corrugation valleys.

Additional details, embodiments, and arrangements of this invention are described in the following "detailed description of the invention."

DETAILED DESCRIPTION OF THE INVENTION

This invention is broadly applicable to any system in which liquid and gas contacting takes place by the formation of a thin film layer upon a contact surface and the diffusion of the gas about the liquid. The contactor may operate as a reactor or an evaporator.

The turbulence induced by the corrugations for the liquid flow may also be useful in the design of falling film evaporators. The turbulence induced by the corrugations can maintain mixing as the fluid flows to overcome laminar flow characteristics that give rise to temperature concentration gradients in the film. The turbulence induced by the corrugations will allow the enriching capacity of the evaporation to continue at high efficiency over the entire length of the contacting surface.

Another highly beneficial use of the reactor arrangement of this invention is in its use as an ethoxilation reactor. In such reactions, the material to be ethoxilated such as an alcohol or an alkylphenol flow down a surface as a thin film layer. Ethylene oxide is circulated as a gas in a cocurrent or countercurrent direction. Close temperature control in such reactions is desired to prevent the formation of unwanted side products. The use of the corrugations of this invention in a flat plate surface promote liquid turbulence and overcome the laminar nature of the flow which induces severe temperature and concentration gradients across the thin film.

The most common example of a reaction system is a sulfonation process which is meant to designate any procedure by which a sulfonic acid group with a corresponding salt or sulfonal halide is attached to a carbon atom. The sulfonation method for which this invention is most broadly suited is the treatment of an organic compound with a gas phase sulfur trioxide. Common starting compounds for this sulfonation reaction include alkyl olefins having 8–30 carbon atoms, alkyl benzenes having 8–15 carbon atoms, and aliphatic alcohols having 8–24 carbon atoms.

The organic compounds enter the reactor in a liquid phase and form a falling thin film in the reaction zone. Typical temperatures for the falling film reactant materials are in the range of 10–45° C. although actual temperatures may vary substantially with the organic material.

The $SO_3$ reactant is introduced into the reaction zone in combination with an inert gas in a concentration of from 1–20 wt-%, and preferably, it is introduced in a concentration of from 3–15 wt-%. Concentrations greater than 20 wt-% are not desirable since the high concentration will introduce temperature peaks associated with instantaneous sulfonation of the hydrocarbon reactants as they enter the contacting channels.

Figure 1:
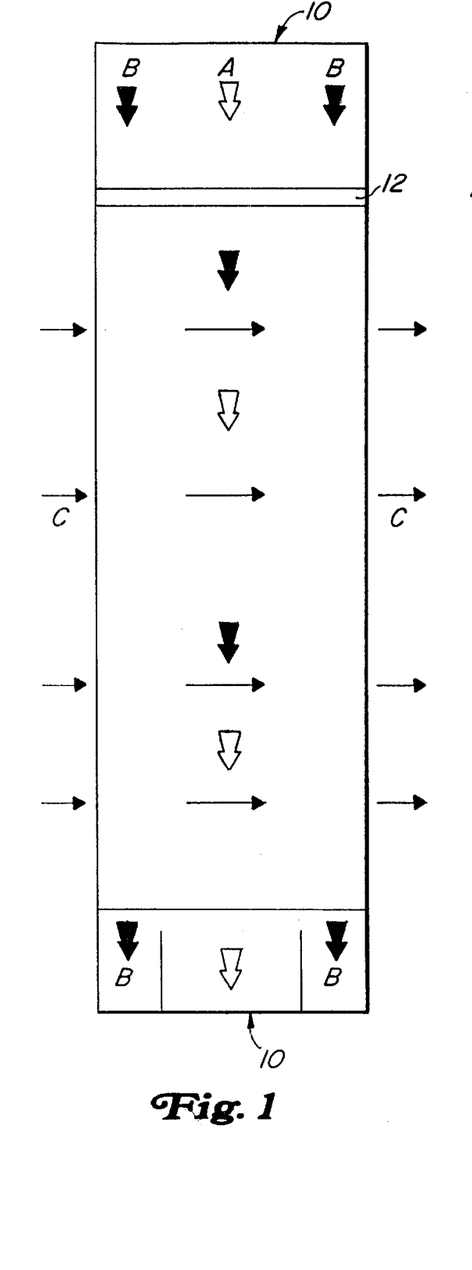
FIG. 1 is a schematic diagram showing a plate reactor of this invention and the direction of process flow streams.
Figure 2:
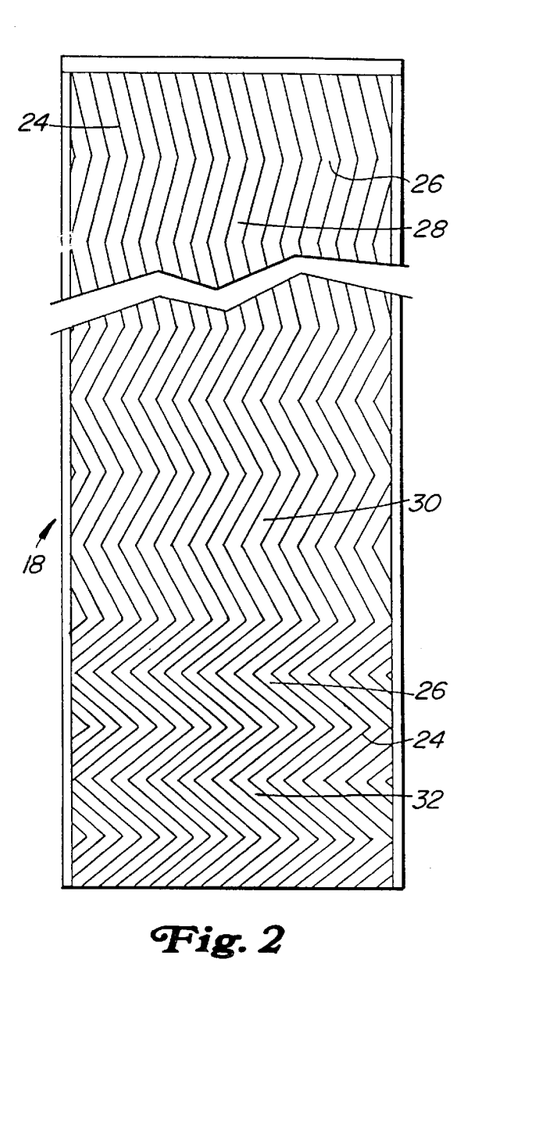
FIG. 2 is a schematic diagram of a corrugated plate for the liquid gas contacting of this invention.
Figure 3:
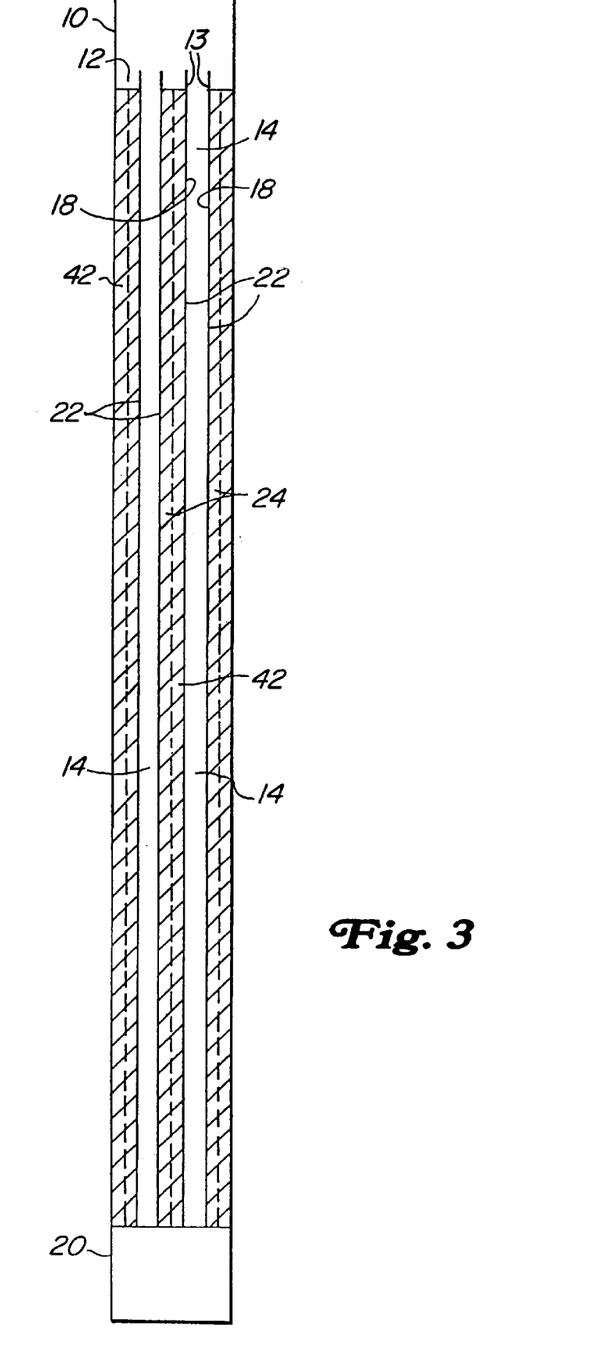
FIG. 3 is a schematic cross-section of a falling film reactor arranged in accordance with this invention.

The general operation of the contactor of this invention may be more fully appreciated from the drawings. FIG. 1 shows a generalized flow arrangement for a falling film liquid reactant and a gaseous reactant that undergoes simultaneous cooling by indirect heat exchange in a reaction zone 10. FIG. 2 schematically shows a typical corrugated plate 18 which in combination with other plates define contacting channels 14 and heat exchange channels 24 as more fully shown in FIG. 3. The liquid, designated by stream B enters the top of the reaction zone and is distributed to the sides of the contacting channels by weirs 12 as shown in FIGS. 2 and 3. Liquid enters the weir system 12 that distributes the liquid across the length of the contacting channel 14. Liquid for distribution down the side of the reactor collects in the weirs defined by dam plates 13 and the closed tops of heat exchange channels 24. Liquid overflowing the weir creates a uniform film passing down the sides 16 of a corrugated plate 18.

The gaseous reactant, shown by stream A in FIG. 1, enters the top of reactor 10 and flows freely down the contacting channels and diffuses into the liquid as it falls over the contacting surface of plate 18. Gas disengages from the liquid in the bottom 20 of reactor 10 for collection of the product stream and recovery and recycle of the gas. The gas phase reactant will usually flow cocurrently with the liquid reactant. However, the gas phase reactant may be introduced to the system for cocurent, countercurrent or cross-current flow.

As shown by FIG. 3, the tops of the heat exchange channels 24 are closed to liquid and gas flow to provide a sealed space for isolated transfer of the heat exchange fluid. The heat exchange fluid, designated by stream C in FIG. 1, is most simply passed through the reaction zone in a transverse direction with the liquid reactants. Suitable manifold structures can distribute and collect the heat exchange fluid from the multiple heat exchange channels at the sides of the reaction zone. Alternately, suitable manifold arrangements for distributing and collecting the heat exchange fluid in a cocurrent or countercurrent flow direction with respect to the liquid reaction are also known.

It is essential to this invention that the plates defining the contacting channel have corrugations formed in their surface. The corrugation pattern for a typical plate 18 as shown in FIG. 2 may be uniform throughout or may vary down the length of the plate as shown in FIG. 2. FIG. 2 shows the corrugation patterns in the idealized fashion with solid lines for the ridges of the corrugations on plate 24 and centralized valley portions 26 between the ridges.

Suitable heat exchange and contacting plates for this invention will comprise any plates which are easily secured in the reaction section in a stable configuration that readily retains the corrugated arrangement. The plates may be formed into curves or other configurations, but flat plates are generally preferred for stacking purposes. Thin plates are ordinarily used and typically have a thickness of from 1–2 millimeters. The lo plates are typically composed of ferrous or non-ferrous alloys such as stainless steels. The general herring bone pattern on the faces of the opposing corrugated plates preferably extends in opposite directions such that the opposing plate faces may be placed in contact with each other to form the flow channels and provide structural support to the plate sections.

The corrugation pattern may be varied to achieve a variety of contacting and reaction effects. Such effects include increased turbulence for improving the contacting between the falling film and the gas phase components and varying the pitch of the corrugation to influence the velocity of the falling liquid as it passes downwardly over the ridges of the corrugations. For example, where rapid heat exchange is desired, the corrugations may extend substantially longitudinally with respect to the fluid flow as shown by section 28 of the drawing. As less cooling is needed, the ridges of the corrugations can be made more transverse to the flow to impede the flow thereby increasing the residence time of the falling film as more of the reaction is completed and less heat is generated. The reduced vertical run and increased pitch for each section of corrugation increases the turbulence of the flowing liquid and improves the diffusion of the gaseous reactant through the liquid reactant.

The transverse component of the ridges may increase continually or in the stepwise fashion as shown in FIG. 2 by sections 28, 30, and 32. As shown by FIG. 2, the channels defined by the corrugations run in a generally vertical direction. Chevron type corrugation arrangements that extend in a substantially horizontal direction should be avoided to prevent concentration of the liquid at the bottom points of the corrugation intersections. The arrangement of vertically continuous flow paths as shown in FIG. 2 keeps the liquid stream dispersed and avoids localized concentration of the liquid.

The degree of turbulence may also be controlled by varying the amplitude of the corrugations and the frequency of the corrugations, which are otherwise referred to as the pitch and the depth of the corrugations. Corrugations having a large pitch or low frequency and shallow depth or low amplitude will provide a low degree of turbulence. Increasing either or both of the frequency and amplitude will raise the degree the turbulence.

It is also essential to this invention that the peaks and valleys of the corrugations defined by adjacent plates are spaced apart by a sufficient distance to prevent substantial contact of the fluid films. Contact between the fluid films as they descend down the plates can cause localized pooling of reactants and undesirable variations in residence time and reactant temperatures. The obstructions formed by the contact of film layers will retard the flow in those film portions through surface tension and frictional losses.

The corrugated plates will usually define heat exchange channels on the side opposite to the film. The heat exchange channels will normally contain a heat exchange fluid. The heat exchange fluid can comprise any fluid having the desired heat exchange and fluid flow characteristics. Plates defining the heat exchange channels preferably contact each other at the high points of the corrugations. Arranging the corrugations in contact, promotes structural stability and support for the heat exchange plates.

Figure 4:
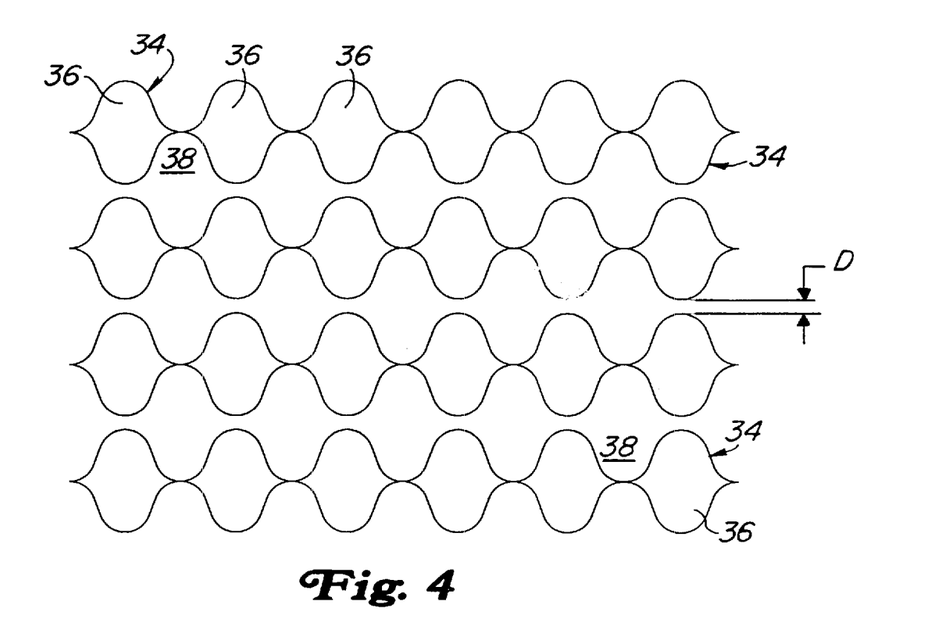
FIG. 4 is a schematic cross-section of contactor channels arranged in accordance with this invention.

FIG. 4 schematically depicts plates 34 into which corrugations are formed for defining heat exchange channels 36 and contacting channels 38. FIG. 4 shows the preferred arrangement where plates 34 are placed to contact adjacent corrugations in the heat exchange channels 36 while the corrugations in the contacting channels 38 are placed apart by a dimension D. The dimension D will vary depending on the process conditions and the properties of the liquid. The dimension D will typically equal at least twice the maximum film layer expected during the operation of the process. The spacing of dimension D may be maintained by use of occasional spacers that contact the points of the corrugations. Such spacers may consist of thin pins that extend over the entire vertical length of the contacting channels or thin bars that extend transversely across the contacting channels.

Figure 5:
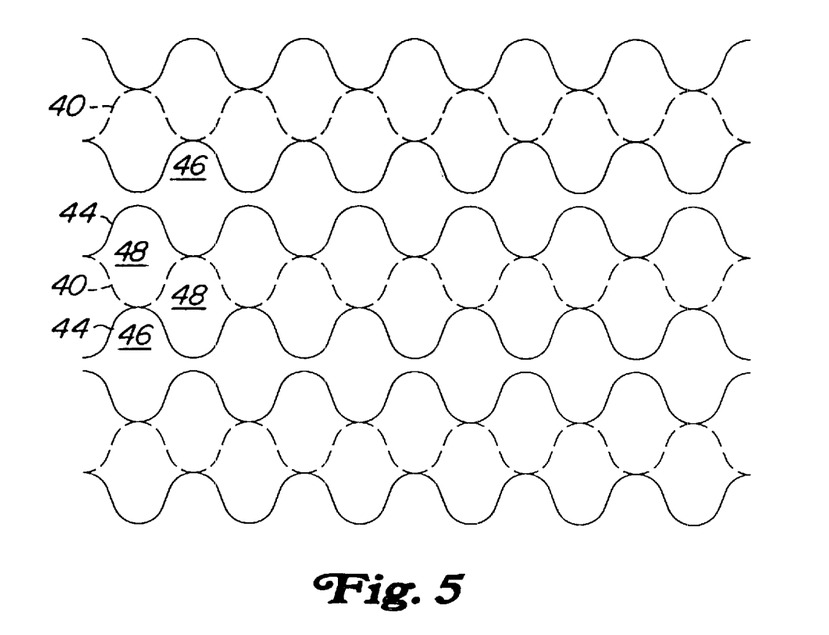
FIG. 5 is a schematic cross-section of a modified contactor channel section arranged in accordance with this invention.
Figure 6:
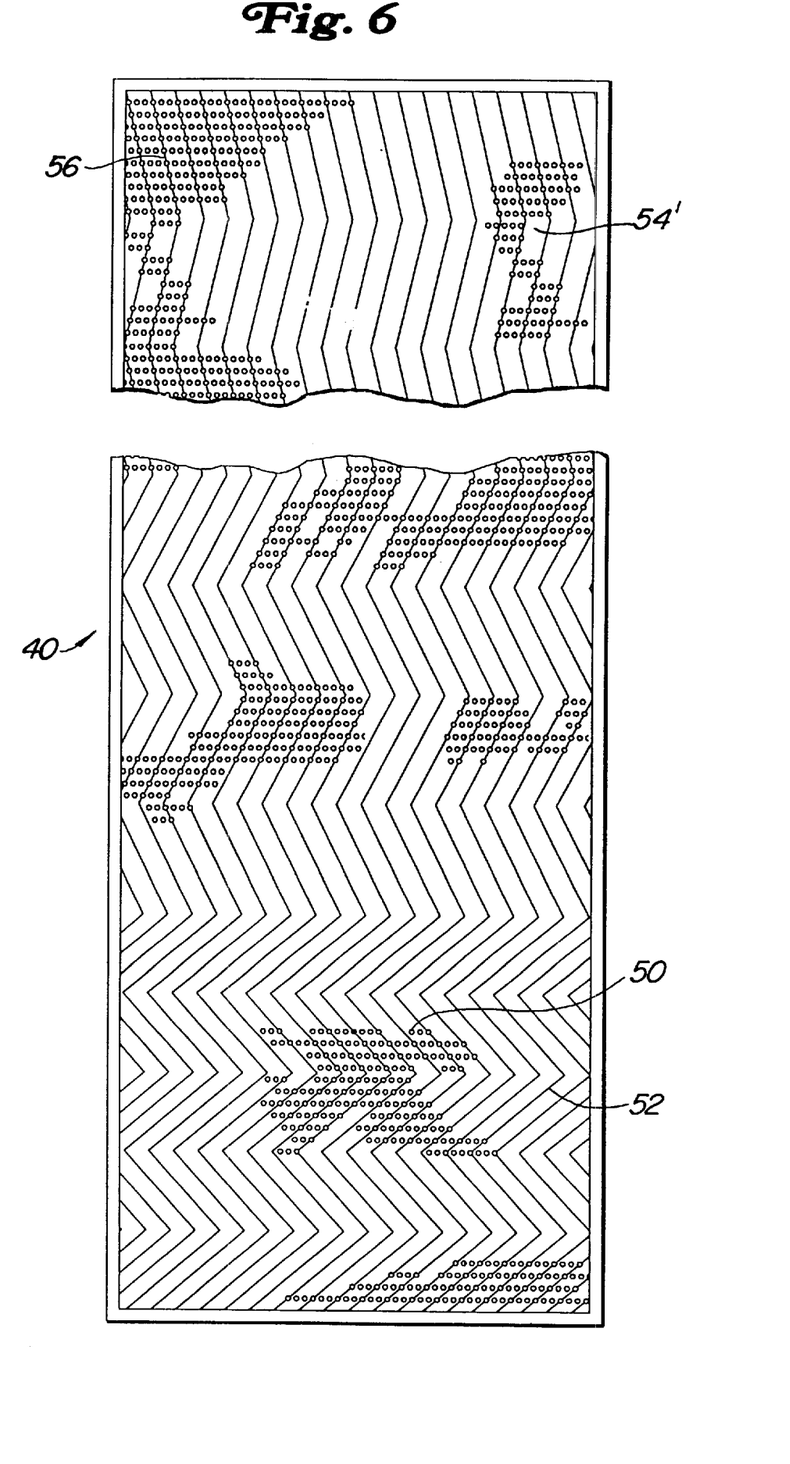
FIG. 6 is a schematic diagram of a perforated plate for the heat transfer channels of this invention.

Flow variations induced by the corrugation pattern can be independently controlled in the contacting channels versus the heat exchange channels. In particular, it may be beneficial to vary the turbulence effect related to the corrugation pattern in the heat exchange channels separately from that of the contacting channels. As shown schematically in FIGS. 3 and 5, this may be accomplished by inserting an additional plate 40 within the heat exchange channels. As shown schematically in FIG. 5, such an arrangement sandwiches plate 40 between plates 44 within heat exchange channels 48. The heat exchange insert plate may be a flat plate with a turbulence inducing structure as shown in U.S. Pat. No. 5,538,700 or a corrugated plate as schematically depicted in FIG. 5. As more clearly illustrated in FIG. 6, the corrugated plate preferably contains perforations 50 between ridges 52 and valleys 54' of the corrugations 56.

The use of the heat exchange insert plate has the additional advantage of facilitating the use of horizontal corrugations in the contacting channels. When the plates define horizontal corrugations, they cannot be placed in contact with each other in the heat exchange channels without blocking flow. Not placing the plates in contact results in a weakened structure. The insertion of a perforated plate between horizontal corrugations maintains the channel for the heat exchange fluid in the heat exchange channel and allows all of the plates to be in contact in the heat exchange channels for improved structural stability.

Figure 7:
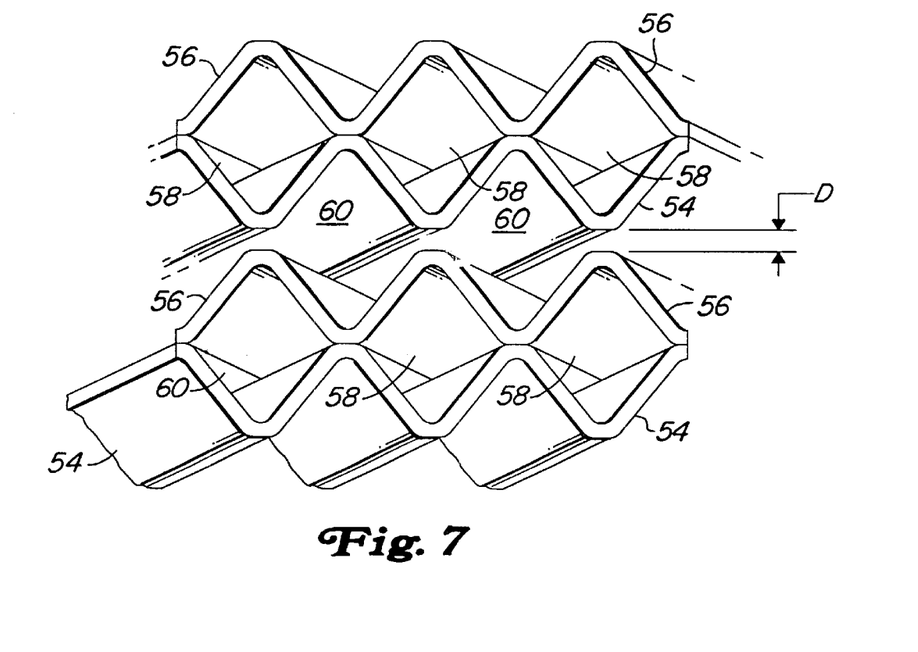
FIG. 7 is a three-dimensional view of a portion of the contacting and heat exchange channels of this invention.

The preferred arrangement of the corrugated plates with a herring bone pattern extending in different directions is more clearly depicted in FIG. 7. Corrugated plates 54 slope generally to the left as they extend downward while corrugated plates 56 extend transversely to the right as they slope downward. Corrugated plates 56 and 54 are placed in contact with each other on one side to define the heat exchange channels 58. On opposite sides, corrugated plates 54 and 56 are again spaced apart by dimension D and form the contacting channels 60.

Figure 8:
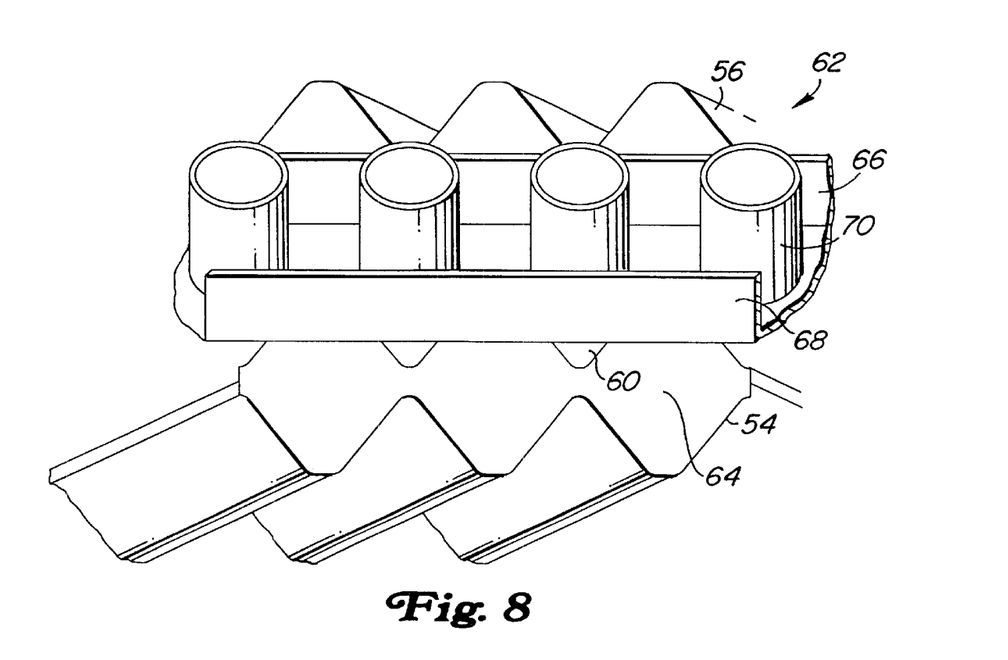
FIG. 8 is a three-dimensional view of a liquid distribution system for supplying liquid to the top of the contacting channels.

FIG. 8 shows one arrangement for a weir system 62 arranged at the top of the corrugations 54 and 56. The weir system distributes liquid to the tops of the corrugation valleys while they also provide open area for gas flow into the channels. The tops of the heat exchange channels defined by plates 54 and 56 are closed by appropriate plugs or sealants over the area 64. The channel system 66 extends over the center of the contacting channels for distributing liquid thereto. The width of liquid channel 66 is less than the width of the contacting channels such that the outermost ends of the channel are left open for fluid to enter the tops of the contacting channels. Liquid overflows the top of channel sidewalls 68 and flows into the outermost section of channel 60. The downward slope of the corrugation distributes liquid as it contacts the angled surface of the corrugations defined by plates 54 and 56. Gas flow into the contacting channels is maintained through the open outer portion of contacting channel 60 and gas risers 70 that extend upwardly from the liquid distribution channel 66. Gas risers 70 are located above the level of sidewalls 68 to prevent liquid from flowing therein.

ILLUSTRATIVE EMBODIMENT

This invention can be used to operate an isothermal sulfonation process for the sulfonation of an alphaolefin with sulfurtrioxide. In such an arrangement, an alpha olefin stream comprising olefins having from 15–18 carbon atoms is formed into a thin film stream by the use of a falling film distributor as depicted in FIG. 8. A stream of $SO_3$ and air flows parallel to the alpha olefins through the contacting channels to effect a reaction. The velocity of the air and $SO_3$ stream is about the same as that of the liquid flowing through the contacting channels. The $SO_3$ containing air stream contains about 7.3 vol-% $SO_3$ and passes through the reactor at a velocity of about 65 m/sec. The film stream passing over the plates is maintained at a temperature of about 50° C. while cooling water passes through the heat exchange channels at a temperature of about 20° C. The flowing film contacting zone has a vertical length of about 2 meters.

What is claimed is:
1. A falling film reactor comprising:
   a) a plurality of corrugated contacting plates positioned in a parallel arrangement to define contacting channels between adjacent plates, said plates defining valleys that extend at least partially in a horizontal direction;
   b) spacing between adjacent plates being sufficient to prevent contact between liquid films on adjacent plates across contacting channels;
   c) means for distributing a liquid medium to the tops of said plates in said contacting channels and producing a thin film of liquid flowing down said plates;
   d) means for passing a gaseous stream through said contacting channels; and,
   e) means for collecting a liquid stream containing a reaction product from the bottom of said contacting channels.

2. The apparatus of claim 1 wherein a first surface of said plates define said contacting channels and a second surface of said plates define heat exchange channels.

3. The apparatus of claim 2 wherein said second surfaces of adjacent plates contact each other.

4. The apparatus of claim 2 wherein a heat exchange plate is positioned between and in contact with the second surfaces of said adjacent plates and said heat exchange plate defines corrugations.

5. The apparatus of claim 4 wherein said heat exchange plates define valleys that extend at an angle with respect to a horizontal that is different than the angle with respect to a horizontal of the valleys defined by said contacting plates.

6. A falling film reactor comprising:
   a) a plurality of corrugated contacting plates positioned in a parallel arrangement to define contacting channels between adjacent plates, said plates defining valleys that extend at least partially in a horizontal direction and define a herring bone pattern;
   b) spacing between adjacent plates being sufficient to prevent contact between liquid films on adjacent plates across contacting channels;
   c) means for distributing a liquid medium to the tops of said plates in said contacting channels and producing a thin film of liquid flowing down said plates;
   d) means for passing a gaseous stream through said contacting channels; and
   e) means for collecting a liquid stream containing a reaction product from the bottom of said contacting channels.

7. The apparatus of claim 6 wherein a first surface of said plates define said contacting channels and a second surface of said plates define heat exchange channels.

8. The apparatus of claim 7 wherein a heat exchange plate is positioned between and in contact with the second surfaces of said adjacent plates and said heat exchange plate defines corrugations.

9. The apparatus of claim 8 wherein said heat exchange plates define valleys that extend at an angle with respect to a horizontal that is different than the angle with respect to a horizontal of the valleys defined by said contacting plates.

10. The apparatus of claim 6 wherein said second surfaces of adjacent plates contact each other.

11. A falling film reactor comprising:
   a) a plurality of corrugated contacting plates positioned in a parallel arrangement to define contacting channels between adjacent plates, each of said plates defining valleys that slope downwardly partially to the left and partially to the right;
   b) spacing between adjacent plates being sufficient to prevent contact between liquid films on adjacent plates across contacting channels;
   c) means for distributing a liquid medium to the tops of said plates in said contacting channels and producing a thin film of liquid flowing down said plates;
   d) means for passing a gaseous stream through said contacting channels; and
   e) means for collecting a liquid stream containing a reaction product from the bottom of said contacting channels.

12. The apparatus of claim 11 wherein a first surface of said plates define said contacting channels and a second surface of said plates define heat exchange channels.

13. The apparatus of claim 11 wherein said second surfaces of adjacent plates contact each other.

14. The apparatus of claim 11 wherein a heat exchange plate is positioned between and in contact with the second surfaces of said adjacent plates and said heat exchange plate defines corrugations.

15. The apparatus of claim 14 wherein said heat exchange plates define valleys that extend at an angle with respect to a horizontal that is different than the angle with respect to a horizontal of the valleys defined by said contacting plates.

* * * * *